United States Patent [19]

Yeh et al.

[11] Patent Number: 4,560,805
[45] Date of Patent: Dec. 24, 1985

[54] CATALYSTS AND PROCESS FOR THE CONVERSION OF OLEFINS TO KETONES

[75] Inventors: Chuen Y. Yeh, Edison; Charles Savini, Warren, both of N.J.

[73] Assignee: Exxon Research & Engineering Co., Florham Park, N.J.

[21] Appl. No.: 516,902

[22] Filed: Jul. 25, 1983

Related U.S. Application Data

[63] Continuation-in-part of Ser. No. 420,527, Sep. 21, 1982, abandoned.

[51] Int. Cl.$^4$ .............................................. C07C 45/42
[52] U.S. Cl. .................................. 568/408; 568/365; 568/309; 568/322; 568/361; 568/404; 568/69; 568/899; 568/900
[58] Field of Search ............... 568/408, 365, 401, 360, 568/320, 309

[56] References Cited

U.S. PATENT DOCUMENTS

| | | | |
|---|---|---|---|
| 2,523,686 | 5/1947 | Engel | 260/597 |
| 3,316,279 | 4/1967 | Fenton | 568/401 |
| 3,389,965 | 6/1968 | de Ruiter et al. | 23/312 |
| 3,471,532 | 10/1969 | Young | 568/401 |
| 3,784,646 | 1/1974 | Holovka et al. | 568/365 |

FOREIGN PATENT DOCUMENTS

| | | | |
|---|---|---|---|
| 641143 | 12/1963 | Belgium | 568/408 |
| 761632 | 9/1933 | France | 568/408 |
| 59179 | 3/1947 | Netherlands | 568/408 |
| 1029175 | 5/1963 | United Kingdom | 568/408 |
| 1054864 | 8/1965 | United Kingdom | 568/408 |
| 52780 | 8/1980 | U.S.S.R. | 568/408 |
| 114924 | 6/1982 | U.S.S.R. | 568/408 |

OTHER PUBLICATIONS

R. H. Blom et al., *Hydrocarbon Proc. & Petr. Refine,* vol. 42, No. 10, pp. 132-134, (Oct. 1963).
R. H. Blom et al., *Ind. & Eng. Chem.,* vol. 54, No. 4, pp. 16-22, (Apr. 1962).
*J. Molec. Catalysis,* vol. 15, pp. 147-156, (1982).
*J. Org. Chem.,* vol. 24, pp. 1847-1854, (1959).
H. S. Broadbent et al., *J.A.C.S.,* vol. 76, pp. 1519-1523, (1954).
H. S. Broadbent et al., *J.A.C.S.,* vol. 81, pp. 3587-3589, (1959).
H. S. Broadbent et al., *J. Org. Chem.,* vol. 27, pp. 4400-4404, (1962).
L. Zanderighi et al., *La Chimica E. L'Industria,* vol. 56, No. 12, 815-820, (Dec., 1964).
*J. Catalysis,* vol. 23, 183-192, (1971).
W. H. Davenport et al., "Advances in Rhenium Catalysis", *Ind. & Eng. Chem.,* vol. 60, No. 11, pp. 10-19, (Nov. 1968).

*Primary Examiner*—James H. Reamer
*Attorney, Agent, or Firm*—J. B. Murray, Jr.

[57] ABSTRACT

An improved process is provided for forming ketones from the corresponding olefins in the vapor phase in the presence of water vapor employing a heterogeneous catalyst comprising rhenium compounds and complexes, optionally containing at least one metal compound or complex selected from the group consisting of Group VIB metals and Group VIII noble metals, and mixtures thereof. It has been surprisingly found that these catalysts effect the formation of ketones in high selectivities with minimal selectivities to the undesirable carbon dioxide and carbon monoxide by-products.

10 Claims, No Drawings

CATALYSTS AND PROCESS FOR THE CONVERSION OF OLEFINS TO KETONES

CROSS-REFERENCE TO RELATED APPLICATIONS

This application is a continuation-in-part of our Ser. No. 420,527, filed Sept. 21, 1982 now abandoned, and is related to our applications filed on even date herewith, Ser. No. 516,903, filed July 25, 1983, now U.S. Pat. No. 4,528,401, entitled "Improved Catalytic Process for the Manufacture of Ketone", which is a continuation-in-part of our Ser. Nos. 420,715 and 420,627, both filed on Sept. 21, 1982; Ser. No. 516,537, filed July 25, 1983, entitled "Catalytic Process for the Manufacture of Ketones", which is a continuation-in-part of our Ser. Nos. 420,525, 420,526, 420,648 and 420,716, all filed on Sept. 21, 1982; and Ser. No. 516,901, filed July 25, 1983, entitled "Improved Catalysts and Process for Oxidative Conversion of Olefins to Ketones", which is a continuation-in-part of our Ser. No. 420,626, filed Sept. 21, 1982.

BACKGROUND OF THE INVENTION

1. Field of the INvention

This invention generally relates to the catalytic vapor phase conversion of olefins to ketones, and to improved catalysts useful therein.

2. Description of the Prior Art

British Pat. No. 1,029,175 to Shell describes a vapor phase olefin oxidation process in which olefins are reacted with $O_2$ at temperatures of less than 350° C. in the presence of water vapor and a halogen, using a supported Group VIII noble metal catalyst containing either an Fe, Ni, Co or Group I or VII transition metal compound, optionally together with an alkali metal compound or one or more transition metal compounds of Groups III–VI. While propylene oxidation is said to give acetone as the main reaction product, such halide-containing systems have severe disadvantages such as the high corrosivity of these systems.

An early patent (U.S. Pat. No. 2,523,686 to W. F. Engel of shell) employs catalysts containing (1) an oxide of a metal of Groups II, III, IV or VI of the Periodic Table and (2) a metal or partially reduced oxide of a metal of Group IB, Group VII or Group VIII of the Periodic Table, and prepares saturated open-ended ketones from olefins of at least three carbon atoms per molecule in a vapor phase process in the presence of steam and under defined conditions. The U.S. patent indicates that Mn is preferred over other Group VII metals (Re and Tc) in the patentee's catalysts. The catalysts are prepared by partial reduction of the metal oxide with $H_2$. Catalyst activity decreases over time, and regeneration of these oxide catalysts are periodically required. Dutch Pat. No. 59,179, also to W. F. Engel, relates to similar catalyst systems.

U.S. Pat. No. 3,389,965 to Shell discloses a process for producing $H_2$ by steam reforming of hydrogen petroleum fractions over a Re-containing catalyst at 400° to 600° C. or higher, which, of course, results in the formation of $CO_2$ and CO in very large amounts. The patent, however, does not relate to the selective, partial oxidation of olefins or alcohols or to the production of ketones and other oxygenated products.

Manganese, another Group VIIB metal, has been investigated in various catalyst systems as a catalyst promoter. L. Zanderighi, et al., *La Chimica E L'Industria*, vol. 56, n. 12, 815–820 (December, 1964) report, for a series of propylene-oxidations to a product mixture of acrolein, acetone, acetaldehyde, propylene oxide and methanol, using various tungstates ($WO_4^-$), of a series of cations, that the reactivities of the tested cations was: $Cu>>Bi>Pb>Fe>Tl>Mn$. Y. Moro Oka, et al., *J. Catalysis*, vol. 23, 183–192 (1971) indicates that no oxygenated products other than carbon oxides were found in propylene oxidation over a $Mn_2O_3$—$MoO_3$ catalyst.

W. H. Davenport et al., "Advances in Rhenium Catalysis", *Ind. & Eng. Chem.*, vol. 60, no. 11, pp. 10–19 (November 1968) states that the chemical and catalytic properties of Re differ considerably from Mn. For example, whereas metallic Mn is highly reactive, slowly decomposes water and reacts with dilute acids, Re metal is relatively inert and does not react with water or nonoxidizing acids. Re catalysts are said to be highly selective hydrogenation catalysts. In the presence of $H_2$, supported or unsupported Re metal preferentially catalyzes the attack by $H_2$ upon carbonyl functions over olefinic bonds, while Re oxides catalyze the saturation of C=C bonds first.

Re-containing hydrogenation catalysts are also disclosed in French Pat. No. 761,632 (1934); H. S. Broadbent et al., *J.A.C.S.*, vol. 76, pp. 1519–1523 (1954); H. S. Broadbent et al., "J. Org. Chem., Volume 24, pp. 1847–1854 (1959); H. S. Broadbent et al., *J.A.C.S.*, vol. 81, pp. 3587–3589 (1959); H. S. Broadbent et al., *J. Org. Chem.*, vol. 27, pp. 4400–4404 (1962).

R. H. Blom et al., *Hydrocarbon Proc. & Petr. Refine*, vol. 43, no. 10, pp. 132–134 (October 1963) and R. H. Blom et al., *Ind. & Eng. Chem.*, vol. 54, no. 4, pp. 16–22 (April 1962) discuss the use of certain Re catalysts in the dehydrogenation of alcohols to aldehydes and ketones.

Rhenium dehydrogenation catalysts are prepared in U.S.S.R. Pat. No. 52,780 (1938), as abstracted at 34 *Chem. Abs.* 5467-7; U.S.S.R. Pat. No. 114,924 (1958), as abstracted at 53 Chem. Abs. 10596f;

Belgian Pat. No. 641,143 (1963) added Re to a supported catalyst containing Fe—Sb oxide on silica to catalyze the oxidation of propylene to acrolein. British Pat. No. 1,038,262 (1966) employed Re oxides to promote supported and unsupported Co and Ni molybdates and Cu phosphate to oxidize propylene to acrolein or acrylic acid.

British Pat. No. 1,054,864 (1967) obtained significant disproportion of 1-butene (62% butene conversion) over 23% $Re_2O_7$ on $Al_2O_3$ (at 150° C., atm. pressure) and a space velocity of 1600, with a 62% butene conversion chiefly to propylene and pentene, albeit with some by-product $C_2$ and $C_6$ olefins. Olefin methanthesis reactions using $O_2$ and Re oxide/alumina catalysts are discussed in R. Nakamura, et al., *J. Molec. Catalysis*, vol. 15, pp. 147–156 (1982) (which is not admitted herein to be prior art to our invention).

Reference is also made to the additional prior art, cited in our co-pending application Ser. No. 516,901, filed July 25, 1983, for catalytic conversion of olefins to unsaturated ketones in the presence of molecular oxygen.

SUMMARY OF THE INVENTION

According to the improved process of this invention, ketones are formed in high selectivities in the vapor phase partial oxidation of olefins in the presence of water vapor and molecular oxygen over a heterogeneous catalyst comprising rhenium complexes and compounds, which can be optionally supported with at least one metal selected from the group consisting of Group VIB metals and Group VIII noble metals and compounds and complexes thereof.

It has been surprisingly found that the catalysts of this invention can provide ketones in very high selectivities, with minimal selectivity loss to the undesirable CO and $CO_2$ by-products.

It has been further found that the catalysts of this invention can effect the above results without the formation of substantial amounts of hydrogenation by-products, such as butane from butene feeds, and such olefin saturation by-products have been detected in the gaseous effluents from the process of this invention in only minimal amounts, if at all.

The process of this invention, in which the ketone is formed in an $O_3$-free reaction zone, also avoids the use of explosive $O_2$-olefin gas mixtures and therefore greatly minimizes the hazards and expense associated with the handling of such $O_2$-olefin gas mixtures.

DETAILED DESCRIPTION OF THE INVENTION

Catalyst

The catalysts of this invention comprise compounds and complexes of Re, preferably in a supported form. The Re can be present in a variety of forms including a compound or complex thereof, alone or in admixture with a suitable promoter for the desired ketone formation reaction. When present as a Re compound, the metal can be chemically combined with an inorganic anion such as oxygen, sulfur and halide (Br, F, Cl or I). Preferred are non-halide Re catalysts such as those selected from the group consisting of Re oxide, Re sulfide and mixtures thereof. Particularly preferred Re oxide and sulfides are $Re_2O_3$, $ReO_2$, $ReO_3$, $Re_2O_5$, $Re_2O_7$, $Re_2S_7$, $ReS_2$, $ReS_3$ and $Re_2S_5$.

The Re catalyst can optionally contain as a promoter a member selected from the group consisting of a metal or metal compound or complex of a Group VI metal, a Group VIII noble metals or a mixture thereof. Thus, also suitable as catalyst for the vapor phase process of this invention are Re catalysts containing, as the metal or as compounds or complexes thereof, any one of Cr, Mo, W, Ru, Rh, Pd, Os, Ir and Pt. These additional elemental components of the catalyst can be present as the metals themselves (that is, in the reduced state) or as compounds or complexes thereof, or as mixtures of the foregoing. Any of the inorganic anions discussed above with respect to Re are also suitable as anions with which the additional Group VIB or Group VIII noble metals can be combined. As with the Re component, the Group VIB and/or noble metal will be preferably present in the non-halide form, e.g., an oxide or sulfide. Illustrative of suitable bimetallic catalysts of this invention are Re-Mo, Re-W, Re-Rh, Re-Cr, Re-Pd, Re-Pt, Re-Ir, Re-Ru and Re-Os oxides and sulfides, and mixtures of the foregoing. Illustrative trimetallic catalysts of this invention are oxides and sulfides of Re-Cu-Ru, Re-Mo-Rh, Re-W-Rh, Re-Mo-Pd, Re-Mo-Os, Re-Mo-Pt, Re-W-Pd, Re-W-Os and mixtures of the foregoing. Especially preferred are oxides and sulfides of Rh-Re-Mo, Pd-Re-Mo and Rh-Re-W.

The Re is preferably present in the promoted catalysts of this invention in a Re:promoter metal weight:-weight ratio of from about 0.0001:1 to 10:1, and more preferably from about 0.01:1 to 1:1. Thus, Re-Mo catalyst will preferably contain from about 0.0001 to 10 parts by weight of Re per part by weight of Mo, and more preferably from about 0.01 to 1 part by weight of Re per part by weight of Mo. Similarly, in Re-Rh-Mo catalysts, the weight ratio of Re:(Rh+Mo) will preferably range from about 0.0001 to 10:1, and more preferably from about 0.01 to 1:1.

The catalysts which are used in the process of the present invention are solids which can be prepared by any of the methods known in the art. Furthermore, they can be employed in any suitable form, or example, as granules, pellets, powders and the like, and they can be either used as such or supported (as is preferred) on or admixed with an inert material, such as alumina, silica, silica-alumina, zeolites, pumice, any of the activated earths, kieselguhr, clays and the like. The preferred support for the catalyst of this invention is alumina, and most preferably gamma-alumina.

Preferred support bimetallic Re catalysts of this invention are those containing from about 0.1 to 10 wt.% Re together with from about 1 to 30 wt.% of a Group VIB metal (e.g., Mo or W), and more preferably those containing from about 1 to 5 wt.% Re, together with from about 3 to 15 wt.% of a Group VIB metal (e.g., Mo or W), calculated as wt.% of the indicated metals based on the total weight of the supported catalyst. Preferred supported trimetallic Re catalysts of this invention are those containing (based on the total weight of the supported catalyst) from about 0.001 to 5 wt.% of a Group VIII noble metal (e.g., Rh, Pd, Pt or Ru), from about 0.1 to 10 wt.% Re together with from about 1–30 wt.% Mo, and, more preferably, those containing from about 0.1 to 1.0 wt.% of a Group VIII noble metal (e.g., Rh, Pd, Pt or Ru), from about 1 to 5 wt.% Re together with from about 3 to 15 wt.% of a Group VIB metal (e.g., Mo or W), calculated as wt.% of the indicated metals based on the total weight of the supported catalyst. Preferred supported trimetallic Re catalysts of this invention are those containing (based on the total weight of the supported catalyst) from about 0.001 to 5 wt.% Rh, from about 0.1 to 10 wt.% Re together with from about 1–30 wt.% Mo, and, more preferably, those containing from about 0.1–1.0 wt.% Rh, from about 1 to 5 wt.% Re, together with from about 3 to 15 wt.% Mo.

Most preferably, the catalyst composition ranges from 1 to 30 wt.% of catalyst metals in relation to the total weight of the supported catalyst.

The supports themselves are preferably characterized by a specific surface area of at least about 10 square meters per gram, and more preferably from about 25 to 200 square meters per gram, (as determined by the BET method), and by a pore volume of at least about 0.1 cc./gm, and preferably from about 0.2 to 1.5 cc./gm (as determined by mercury porosimetry).

The catalysts can themselves be formed from a thermally decomposable salt so that a suitable solution of the selected rhenium salt, for example, can then be impregnated on to the surface of a catalyst support followed by calcining at a temperature of at least about 400° C. for sufficient time to activate the catalyst. Generally, a time of from about 1 to 5 hours will be sufficient at a temperature within the range of 300° to 600° C. This calcining step can be performed in air or in the presence of $H_2S$ or an inert gas such as nitrogen, helium and the like. The particular decomposable compound selected will influence the anion associated with the Re and promoter cations in the supported catalyst following the calcining step. Thus, a thio-salt of Re and/or promoter, such as ammonium thiorhenates or ammonium thiomolybdates, will be generally calcined to form a Re sulfide catalyst. Non-thio salts, such as the nitrate, carboxylates, carbonate and the like which do not contain S, will generally yield a Re oxide catalyst on decomposition when the decomposable salt itself contains oxygen or when the calcining is conducted in an $O_2$-containing gas (e.g., air). Similarly, calcining the above S-free Re and promoter salts in the presence of an $H_2S$, COS, or $CS_2$ atmosphere will also provide a catalyst containing Re sulfides.

The selected catalyst components (e.g., rhenium salt such as ammonium perrhenate, the mono- or di-carboxylate of from 1 to 10 carbon atoms (e.g., the acetate, oxalate and the like), carbonate, nitrate and the like, alone or in combination with a selected promoter compound (e.g., ammonium permolybdate) are intimately mixed in the presence of a solvent so as to produce a solution or for a flowable paste. Then the selected support is impregnated with this liquid mixture and evaporation is carried out under the selected temperature conditions to obtain a dry solids. Water may be used as the solvent for mixing the catalyst components, but oxygenated organic compounds such as alcohols, ethers, esters, dioxane and the like can also be used.

A particularly preferred catalyst of this invention is prepared by first depositing (e.g., by vacuum impregnation) the selected support (e.g., gamma-alumina) with a thermally decomposable molybdenum compound (e.g., ammonium permolybdate or thiomolybdate), followed by drying and calcining to form solids having molybdenum salts deposited thereon. Thereafter, the selected decomposable rhenium compound (e.g., ammonium perrhenate) is deposited thereon, e.g., by vacuum impregnation, followed by a second drying and calcining of the solids. If desired, a Group VIII noble metal promoter compound (e.g., a rhodium salt such as rhodium nitrate) can then be deposited on the Mo-Re catalyst, again followed by drying and calcining. Alternatively, the preferred catalyst can be prepared by depositing the selected Group VIII noble metal promoter compound prior to, or simultaneously with, the deposition of the Re compound onto the surface of the solids on which molybdenum has been previously deposited. Each drying step can be performed at temperatures within the range of from about 100° to 300° C. for a time sufficient to remove substantially all water (in the case of use of aqueous solutions of the foregoing Mo, Re and/or Group VIII noble metals salts) or at a temperature above the solvent boiling point to about 300° C., for removal of any other selected solvent used during the impregnation or deposition of the metals, optionally together with passing of an inert gas such as nitrogen over the solids' surface to facilitate the removal of the water or solvent. The calcining temperatures and times are as described above.

Formation of especially preferred supported Mo sulfide solids from thermally decomposable thiomolybdate compounds is more completely described in our co-pending applications, Ser. Nos. 420,715 and 420,627, filed Sept. 21, 1982, whose disclosures are hereby incorporated by reference.

The supported catalyst thus prepared will generally have a surface area of at least about 5 m$^2$/gm (and preferably at least 40 m$^2$/gm) and can be used in a fixed bed and can also be used in fluidized bed or other conventional means of housing the catalyst particles for ultimate contact with the gaseous reactants.

Olefin Conversion Process

The olefinic hydrocarbons which can be employed as reactants in the process of this invention are those which contain an aliphatic chain of at least two carbon atoms in which there exists at least one aliphatic double bond, —HC=CH—. Suitable olefinic hydrocarbons are those which are normally gaseous as well as those which are liquids at room temperatures but which can exist in the gaseous form at the elevated temperature and pressure conditions which are employed during the reaction. Representative olefinic reactants which can be employed, either alone or in combination, are propylene, 1-butene, 2-butene, 1-pentene, 2-pentene, 1-hexene, 2-hexene, 3-hexene, 3-methyl-1-pentene, cyclobutene, 1-heptene, 2-heptene, 1-octene, 2-octene, 1-nonene, 2-nonene, 1-decene, cyclohexene, cyclooctene, 1-dodecene, 1-hexadecene, allyl benzene, propenyl benzene, 3-phenyl-1-hexene, 4-o-tolyl-1-butene, and 1,6-diphenyl-3-hexene. Thus, suitable olefins include (1) linear mono olefins of 2 to 20 carbon atoms, inclusive of terminal olefins, i.e., olefins, having a terminal $H_2C$=CH— group, and internal olefins having the carbon-carbon double bond, as a —HC=CH— group in an internal carbon-carbon bond of the olefin, and (2) cyclic mono-olefins of 4 to 20 carbon atoms having a —HC=CH— group in the cyclic ring. Particularly suitable for this invention are alkenes having from 2 to 10 carbon atoms and cycloalkenes of 4 to 10 carbon atoms, and most preferred are linear alkenes having from 4 to 10 carbon atoms. Illustrative of these preferred classes of olefin feeds are those comprising 1-butene, 2-butene, 1-hexene, 1-pentene, propene, 1-octene, cyclohexene, cyclopentene, cyclobutene and the like, and mixtures thereof.

Paraffins (such as alkanes of 2 to 20 carbon atoms) and isoolefins (i.e., olefins having a >C=C< group in which one or both carbon atoms are hydrocarbyl substituted, such as 2-methyl-2-butene) can be also present in the gas feed to the oxidation zone in the practice of this invention, but they are essentially unreactive in forming the desired ketones.

Preferred olefinic feeds are olefin gas mixtures obtained from the refining of crude oil. Thus, butene cuts from such refineries typically contain n-butenes (1-butene and 2-butene) which will be converted by this process into 2-butanone, and also typically contain butane and isobutene.

The process of this invention is effected by passing the selected olefin and water vapor over the surface of a catalyst of this invention under conditions such as to maintain a vaporous olefin in the reaction zone. The conditions of temperature and pressure under which this can be performed can vary widely depending on such factors as the particular olefin selected for use, the space velocity of gases through the reactor and other factors. Generally, however, a temperature of from about 125° to 600° C., preferably from about 200° to less than about 400° C., will be entirely suitable. Most preferably, where the alkene comprises butene-1 or butene-2, the temperature within the catalyst reactor is maintained within the range of from about 250° to 375° C. Similarly, for cycloalkenes such as cyclohexene, a temperature range of about 125° to about 200° C. is most preferable. The pressures are in no way critical and will generally range from about 0 to 2000 psig, preferably from about 5 to 150 psig, although higher or lower pressures are also suitable.

The space velocity of the total gases through the oxidation reactor are also not critical and can range from 100 to 10,000 v/v/hr., and preferably from about 200 to 6,000 v/v/hr., where "v" represents a unit of volume (e.g., "cc").

The reaction can be carried out either batchwise, continuously, or semi-continuously. In batch operations, the gaseous reactants may be placed, together with the catalyst, in a suitable pressure vessel and allowed to remain there under the desired reaction conditions for a suitable reaction interval, which will generally range from about 0.01 to 10 hours or more, depending on the degree of reaction completeness sought. In continuous operation, the gaseous reactants are passed through a body of the catalyst supported within a reactor vessel, which can be any of the conventional equipment employed by the industry for such reactions.

The water vapor can be combined and premixed with, or introduced separately from, the olefin feed, or they can be passed to the reaction vessel via separate conduits. The manner of contacting the water vapor and olefin is not critical and any of the conventional gas-gas contacting methods employed in the industry may be used.

The ratio of olefin:water vapor can also vary widely. Generally, the molar ratio of olefin:water vapor introduced to the reactor will range from about 2:1 to 1:20, preferably from about 1:1 to 1:10. However, ratios outside the foregoing ranges can also be employed.

An inert gaseous diluent such as nitrogen or paraffin can also be introduced together with the other gaseous feeds to the reactor in order to achieve a desired high space velocity and to minimize hot spots which could result in an over-oxidation of the feed and/or reactants during the exothermic ketone formation.

Preferably, the olefin and water vapor are contacted with a non-halide catalyst of this invention and in the substantial absence of free halide (that is a molar ratio of free halide:olefin of less than about $1 \times 10^{-5}:1$) in order to minimize corrosion difficulties.

The reaction zone, in which the desired reaction between the olefin and water vapor to form the selected ketone is effected, is preferably oxygen-free, that is, contains a molar ratio of added molecular oxygen to olefin of less than about 0.01:1. Molecular oxygen, therefore, is not a desired component of the gas feed to the process and its presence serves to increase the amount of oxygenated by-products, including carbon dioxide and carbon monoxide, as will be illustrated in the examples which follow.

The gas feed is preferably substantially free of $H_2S$, e.g., contains less than about 0.01 vol.% $H_2S$, to avoid complicating the task of product recovery and purification.

The ketones which are formed will depend, of course, on the particular olefin(s) employed in the feed. Thus, use of alkene as the olefin will result in forming the corresponding alkanone having the same number of carbon atoms as the alkene fed (acetone from propylene; methyl ethyl ketone from 1-butene, 2-butene, or mixtures thereof; cyclohexanone from cyclohexene). The process is particularly suitable for forming alkanones having from 4 to 10 carbon atoms.

The major alcohol product formed in the process of this invention will correspond to the carbon skeleton of the ketone product, e.g., secondary butyl alcohol corresponding to methyl ethyl ketone.

The ketones and alcohols produced by the process of this invention can be recovered from the reaction mixture in any desired manner, such as by distillation or by extraction with water or other solvents followed by distillation. Preferably, at least a portion of the unreacted gases are recovered and recycled to the reactor in addition to fresh feed gases in order to maximize olefin conversion. Alternatively, a series of reactor vessels can be employed and the unreacted gases from the first vessel can then be passed as feed to the second vessel, together with make-up gaseous olefin and water vapor as required.

Gaseous $H_2$, which is also formed in the overall reaction, illustrated by equation (I) below, can be readily recovered from the reaction effluents.

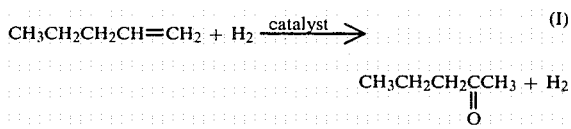

$$CH_3CH_2CH_2CH=CH_2 + H_2 \xrightarrow{catalyst} \quad (I)$$

$$CH_3CH_2CH_2\underset{\underset{O}{\|}}{C}CH_3 + H_2$$

While not wishing to be limited thereby, it is believed that the ketone product formed by the process of this invention proceeds by way of an alcohol intermediate corresponding to the skeleton structure of the ketone product. It is believed that this is the explanation for the quantity of alcohol product which is also formed and detected in the examples that follow. For example, butene is converted to a mixture of ketone and secondary butyl alcohol. Accordingly, our invention also provides a process for contacting such an alcohol with water vapor in the presence of a catalyst of this invention to form a corresponding ketone. Process parameters include feed ratios, reaction times, space velocities, temperatures, pressures and the like, which are discussed above for the use of olefin-containing feeds, are also useful in the embodiment of this invention in which the alcohol is employed as the feed. The molar ratio of alcohol:water vapor is generally from about 0.01:1 to 100:1, and preferably from about 0.01:1 to 10:1. Alcohols which are suitable as feeds correspond to any of the above-discussed product alcohols of this invention. Therefore, particularly suitable are alkanols, and especially secondary alkanols, having from 3 to 10 carbon atoms per molecule. The utility of the catalysts of this invention for conversion of alcohols to ketones can be readily seen from the following examples, and it will also be apparent to one skilled in the art that recycle of recovered alcohol by-product to an olefin-reaction zone using a catalyst of this invention will provide improved overall utilization of an olefin-containing feed as a result of the further reaction of the thus-recycled alcohol by-product.

The process of this invention can be further illustrated by reference to the following examples wherein percent conversions and selectivities are mole percent.

Product selectivities in the examples were determined by gas chromatographic analysis after steady-state conditions were observed. Products formed were methyl ethyl ketone, CO, $CO_2$, secondary butyl alcohol, butyl mercaptan and the balance unknowns. In the Examples 1-9 and 14-18, the gaseous effluents from the reactor were analyzed for butene consumed, using isobutane as a standard and employing response factors determined for the GC by calibration with a known gas mixture. In Examples 10-13, the gaseous reactor effluent was passed through a series of four traps partially filled with water. The solutions in each trap were analyzed by gas chromatography using dioxane as internal standard. No internal standard was employed in Example 14.

To illustrate the surprisingly improved selectivities to methyl ethyl ketone which are achieved in the process of this invention and the substantial absence of oxygen, a trimetallic rhenium-rhodium-molybdenum sulfide catalyst of this inventiom was prepared and then tested in oxide form in the presence of molecular oxygen to establish a base line of activity. Thereafter, this oxide catalyst was converted to a sulfide form and then tested in the presence of molecular oxygen for a butene feed to determine a base line of activity. Thereafter, a series of subsequent runs were conducted in which molecular oxygen was not employed as a component of the gas feed.

EXAMPLE 1

Catalyst Preparation (a) Vacuum Impregnation

Gamma-alumina (30 cc.; 12–20 mesh; 100 m$^2$/gm surface area; 0.45 cc./gm pore volume; Alfa Products) was dried in air in a Linberg furnace at 500° C. for 3 hours to give a dry weight of 26.4 grams. Ammonium paramolybdate [(NH$_4$)$_6$Mo$_7$O$_{24}$.4H$_2$O] (4.63 grams) was dissolved in distilled water to form a 10.6 cc. aqueous solution and transferred into a 60 cc. dropping funnel. The catalyst support was placed in a 125 cc. glass filtering flask equipped with a side arm for pulling a vacuum, and the filtering flask was attached to a dropping funnel using a rubber stopper. After evacuation to a pressure of −15 in Hg, the ammonium paramolybdate solution was added dropwise to the catalyst support to achieve complete wetness. The impregnated wet catalyst was placed in a stainless steel gauze boat and dried in air at 125° C. for 1 hour, 250° C. for 1 hour and 350° C. for 1 hour, and finally calcined in air by raising the furnace temperature to 500° C. (at a rate of about 10° C./min.), which was maintained for 3 hours. After cooling to room temperature, the solids were then impregnated with 10.3 cc. of an aqueous solution containing 1.41 grams of ammonium perrhenate, after which the same four-step drying and calcining procedure was used. Finally, these solids were impregnated with a 10.3 cc. aqueous solution containing 0.57 grams of Pd(NO$_3$)$_2$, again followed by the same four-step drying and calcining procedure. The thus-produced solids were found to comprise mixed oxides of palladium, rhenium and molybdenum and to contain 1.0 wt.% Pd, 3.7 wt.% Re, and 9.5 wt.% Mo, calculated as the respective elements, based on the weight of the catalyst support.

(b) Sulfiding Procedure

Ten cc. of the foregoing oxide catalyst and 20 cc. of fused ceramic inerts (12–20 mesh) were well mixed and loaded into a test reactor which comprised a 24-inch (0.38 inch ID) stainless steel tubular reactor equipped with gas inlets and gas outlets at opposing ends of the tubular reactor. The reactor was then heated to a temperature of 325° C. (which was maintained by means of electric heating tape and a Gardsman temperature control). Temperatures in the reactor were determined by means of a thermocouple positioned in the center of the catalyst bed. A gas mixture of hydrogen sulfide (190 cc./min.; charged as 6 vol.% H$_2$S in N$_2$) and H$_2$ (230 cc./min.) was charged to the reactor at a gas inlet pressure of 9 psig, for 3 hours, to convert the oxide catalyst to the sulfide form. The resulting solids were then contacted under the same flow conditions with H$_2$ (520 cc./min.) to strip out any absorbed, unreacted H$_2$S. The catalyst was then determined to comprise a mixture of rhenium sulfide, palladium sulfide, and molybdenum sulfide, and to contain 1.0% Pd, 3.7% Re and 9.5% Mo, calculated as the respective elements, based on the total weight of the catalyst support.

EXAMPLE 2 FOR COMPARISON

To determine the performance of the catalyst prepared in Example 1(b) in the presence of an O$_2$-containing feed, a gaseous mixture of the following composition, containing butene-1, oxygen, nitrogen and water vapor was passed to the reactor described in Example 1(b): 380 cc./min. of a 10:90 vol:vol mixture of oxygen:nitrogen; 60 cc./min. of a gas mixture containing 85 vol.% butene-1 and 15 vol.% iso-butane; and 224 cc. per minute of water vapor. The total gas hourly space velocity of the gaseous mixture through this reactor was 3984 cc/cc/hr. A gaseous inlet pressure of 9.7 psig and a temperature of 310° C. was employed throughout the reaction (1.2 hrs.). A gaseous effluent was continuously withdrawn from the reactor and was sampled and analyzed by means of an on-line gas chromatograph. After achieving steady conditions, methyl ehtyl ketone was found to have been formed in a selectivity of about 58.3% at a butene conversion of 6.5%. The following by-product selectivities were observed: 11.3% CO$_2$, 5.0% CO, 5.3% secondary butyl alcohol and 14.0% secondary butyl mercaptan.

EXAMPLE 3

In a series of separate runs, the Re-Mo-Pd sulfide catalyst used in Comparative Example 2 was contacted with a butene feed under the conditions indicated in Table I below, except that no oxygen was passed to the reactor. The data thereby obtained are set forth in Table I.

TABLE I

| | | | | Gas Feed (cc/min.) | | | | | % Selectivities to: | | | | | |
|---|---|---|---|---|---|---|---|---|---|---|---|---|---|---|
| Run No. | Time (hrs) | Temp. (°C.) | Press. psig | Butene (1) | H$_2$O | N$_2$ | GHSV (2) | Butene Conv. (%) | MEK (3) | CO$_2$ | CO | SBA (4) | C$_4$SH (5) | Total Product (MEK + SBA) |
| 1 | 4.0 | 304 | 9.2 | 60 | 224 | 380 | 3984 | 1.8 | 93.1 | 0 | 0 | 6.3 | 0 | 99.4 |
| 2 | 6.4 | 297 | 9.4 | 31 | 224 | 170 | 2550 | 2.5 | 95.1 | 0 | 0 | 4.9 | 0 | 100.0 |
| 3 | 10.1 | 365 | 9.2 | 60 | 224 | 380 | 3984 | 2.0 | 97.6 | 0 | 0 | 2.3 | 0 | 99.9 |
| 4 | 12.0 | 367 | 9.5 | 104 | 224 | 730 | 6336 | 2.4 | 97.3 | 0 | 0 | 1.9 | 0 | 99.2 |

TABLE I-continued

| Run No. | Time (hrs) | Temp. (°C.) | Press. psig | Gas Feed (cc/min.) Butene (1) | H$_2$O | N$_2$ | GHSV (2) | Butene Conv. (%) | % Selectivities to: MEK (3) | CO$_2$ | CO | SBA (4) | C$_4$SH (5) | Total Product (MEK + SBA) |
|---|---|---|---|---|---|---|---|---|---|---|---|---|---|---|
| 5 | 12.8 | 371 | 9.7 | 60 | 224 | 0 | 1704 | 2.8 | 95.0 | 0 | 0 | 4.2 | 0 | 99.2 |

(1) Feed = gas mixture containing 85 vol. % butene-1 and 15 vol. % n-butane.
(2) Total gas hourly space velocity.
(3) Methyl ethyl ketone.
(4) Secondary butyl alcohol.
(5) Butyl mercaptan.

EXAMPLE 4

Fifteen cc. of the palladium-rhenium-molybdenum oxide catalyst prepared in Example 1(a) was further vacuum impregnated using the procedure of Example 1(a) with a 5.1 cc. aqueous solution containing 0.069 gram of sodium nitrate, followed by the four-step drying and calcining procedure employed in Example 1(a). The resulting solids were found to additionally contain 0.1 wt.% Na, calculated as the element, based on the weight of the total catalyst support, in addition to the 1.0% Pd, 3.7% Re, and 9.5% Mo. This catalyst was then mixed with inerts and sulfided using the procedure set forth above in Example 1(b), and the resulting sulfided catalyst was then employed in a series of runs following the procedure of Comparative Example 2 under the conditions summarized in Table II below.

TABLE II

| Run No. | Time (hrs) | Temp. (°C.) | Press. psig | Gas Feed (cc/min.) (1) 1-Butene | O$_2$/N$_2$ (2) | H$_2$O | N$_2$ | GHSV (3) | Butene Conv. (%) | % Selectivities MEK (4) | CO$_2$ | CO | SBA (5) | C$_4$SH (6) | Total Product (MEK + SBA) |
|---|---|---|---|---|---|---|---|---|---|---|---|---|---|---|---|
| 1 | 0.7 | 304 | 9.4 | 60 | 380 | 224 | 0 | 3984 | 10.8 | 39.8 | 13.5 | 14.6 | 2.8 | 1.4 | 42.6 |
| 2 | 3.2 | 298 | 9.7 | 60 | 0 | 224 | 380 | 3984 | 1.6 | 92.2 | 0 | 0 | 7.8 | 0 | 100.0 |
| 3 | 6.6 | 294 | 9.7 | 104 | 0 | 224 | 730 | 6336 | 2.2 | 95.4 | 0 | 0 | 4.6 | 0 | 100.0 |
| 4 | 12.7 | 372 | 7.2 | 60 | 0 | 224 | 0 | 1704 | 5.2 | 96.8 | 0 | 0 | 2.4 | 0 | 99.2 |

(1) Feed = gas mixture containing 85 vol. % butene-1, 15 vol. % n-butane.
(2) Fed as 10 vol. % O$_2$ in N$_2$.
(3) Total gas hourly space velocity.
(4) Methyl ethyl ketone.
(5) Secondary butyl alcohol.
(6) Butyl mercaptan.

EXAMPLE 5

Following the procedure of Example 1(a), 26.4 grams of dry gamma-alumina was sequentially impregnated with Mo (using 10.6 cc. of an aqueous solution containing 4.62 grams of ammonium paramolybdate), Re (using 10.3 cc. of an aqueous solution containing 1.42 grams of ammonium perrhenate), and finally by Rh (using 10.3 cc. of an aqueous solution containing 0.37 gram of rhodium trinitrate). After each impregnation, the solids are dried under air at 125° C. for 1 hour, 250° C. for 1 hour, and 350° C. for 1 hour, and then calcined under air at 500° C. for 3 hours. The resulting oxide catalyst was found to comprise 0.5 wt.% Rh, 3.7 wt.% Re, and 9.7 wt.% Mo, calculated as a respective element, based on the total weight of the support. The oxide catalyst was mixed with inerts and sulfided using the procedure of Example 1(b), and the resulting sulfided catalyst was employed in a series of runs following the procedure of Comparative Example 2 using conditions set forth in Table III.

TABLE III

| Run No. | Time (hrs) | Temp. (°C.) | Press. psig | Gas Feed (cc/min.) (1) 1-Butene | O$_2$/N$_2$ (2) | H$_2$O | N$_2$ | GHSV (3) | Butene Conv. (%) | % Selectivities MEK (4) | CO$_2$ | CO | SBA (5) | C$_4$SH (6) |
|---|---|---|---|---|---|---|---|---|---|---|---|---|---|---|
| 1 | 0.6 | 315 | 9.0 | 60 | 380 | 224 | 0 | 3984 | 12.0 | 65.3 | 22.7 | 3.4 | 1.3 | 4.1 |
| 2 | 2.7 | 301 | 9.5 | 104 | 730 | 224 | 0 | 6336 | 14.0 | 56.5 | 20.7 | 13.0 | 1.1 | 1.9 |
| 3 | 4.2 | 310 | 9.2 | 60 | 0 | 224 | 380 | 3984 | 2.3 | 96.9 | 0 | 0 | 1.1 | 2.0 |
| 4 | 6.2 | 306 | 9.4 | 104 | 0 | 224 | 730 | 6336 | 3.5 | 98.2 | 0 | 0 | 0 | 1.8 |
| 5 | 6.8 | 301 | 9.0 | 31 | 0 | 224 | 170 | 2550 | 3.8 | 98.2 | 0 | 0 | 1.0 | 0.9 |
| 6 | 7.8 | 376 | 9.4 | 31 | 0 | 224 | 170 | 2550 | 8.6 | 93.5 | 0 | 0 | 1.1 | 5.0 |
| 7 | 8.3 | 375 | 9.4 | 60 | 0 | 224 | 380 | 3984 | 6.4 | 98.0 | 0 | 0 | 0 | 2.0 |
| 8 | 8.8 | 375 | 9.4 | 104 | 0 | 224 | 730 | 6336 | 6.5 | 97.1 | 0 | 0 | 0 | 2.9 |
| 9 | 12.8 | 386 | 9.1 | 60 | 0 | 224 | 0 | 1704 | 12.6 | 98.4 | 0 | 0 | 0.8 | 0.8 |

(1) Feed = gas mixture containing 85 vol. % butene-1, 15 vol. % n-butane.
(2) Fed as 10 vol. % O$_2$ in N$_2$.
(3) Total gas hourly space velocity.
(4) Methyl ethyl ketone.
(5) Secondary butyl alcohol.
(6) Butyl mercaptan.

EXAMPLE 6

The catalyst preparation procedure of Example 5 is repeated except that the catalyst solids, following the last calcining step, were then impregnated with 10.3 cc. of an aqueous solution containing 0.11 gram of sodium nitrate. These impregnated solids, containing 0.1 wt.% Na, 0.5 wt.% Rh, 3.7 wt.% Re and 9.5 wt.% Mo (calculated as metals, based on support) were then dried and calcined in air using the procedure of Example 5, and mixed with inerts and sulfided in the reactor employing the procedure of Example 1(b). Thereafter, the sulfided catalyst was used in a series of runs using the procedure of Comparative Example 2. The data thereby obtained are set forth in Table IV.

TABLE IV

| Run No. | Time (hrs) | Temp. (°C.) | Press. psig | Gas Feed (cc/min.) | | | | GHSV (3) | Butene Conv. (%) | % Selectivities | | | | |
|---|---|---|---|---|---|---|---|---|---|---|---|---|---|---|
| | | | | (1) 1-Butene | $O_2/N_2$ (2) | $H_2O$ | $N_2$ | | | MEK (4) | $CO_2$ | CO | SBA (5) | $C_4SH$ (6) |
| 1 | 0.7 | 285 | 9.1 | 60 | 380 | 224 | 0 | 3984 | 11.9 | 60.2 | 28.8 | 0 | 0.9 | 4.0 |
| 2 | 1.8 | 295 | 9.2 | 104 | 730 | 224 | 0 | 6336 | 14.5 | 46.3 | 22.8 | 12.0 | 0.3 | 4.6 |
| 3 | 2.4 | 294 | 9.1 | 60 | 0 | 224 | 380 | 3984 | 2.2 | 96.3 | 0 | 0 | 0 | 3.7 |
| 4 | 7.5 | 300 | 9.0 | 31 | 0 | 224 | 170 | 2550 | 6.3 | 95.4 | 0 | 0 | 0.7 | 3.9 |
| 5 | 9.5 | 357 | 9.0 | 31 | 0 | 224 | 170 | 2550 | 11.0 | 95.7 | 0 | 0 | 1.1 | 3.2 |
| 6 | 11.8 | 375 | 9.1 | 60 | 0 | 224 | 380 | 3984 | 2.9 | 97.3 | 0 | 0 | 1.0 | 1.8 |

(1) Feed = gas mixture containing 85 vol. % butene-1, 15 vol. % n-butane.
(2) Fed as 10 vol. % $O_2$ in $N_2$.
(3) Total gas hourly space velocity.
(4) Methyl ethyl ketone.
(5) Secondary butyl alcohol.
(6) Butyl mercaptan.

EXAMPLE 7

The catalyst preparation procedure of Example 1(a) was repeated employing 12.95 grams of the dry gamma-alumina support, and two impregnations: the first using a 5.3 cc. aqueous solution containing 1.16 grams of ammonium paramolybdate; and the second using a 5.3 cc. aqueous solution containing 0.35 gram of ammonium perrhenate and 0.18 gram of rhodium trinitrate, in that order. After each vacuum impregnation the interstage, four-step drying/calcining procedure of Example 1(a) was repeated, under $N_2$ after the first impregnation and under air thereafter. The resulting oxide catalyst was found to contain 0.5 wt.% Rh, 0.85 wt.% Re, and 4.75 wt.% Mo, calculated as the respective elements, based on the weight of the gamma-alumina support. After mixing this oxide catalyst with inerts as in Example 1(b), the catalyst was subjected to the in situ sulfiding procedure of Example 1(b) and then tested as in Example 6, providing the data summarized in Table V.

weight of 13.4 grams. Ammonium tungstate (1.753 grams, $(NH_4)_{10}W_{12}O_4.5H_2O$) was dissolved in water to make a 27 cc. solution, which was observed to contain some undissolved solids. In a first impregnation, approximately 5.3 cc. of this aqueous solution was impregnated onto the dried solid, after which the impregnated solids were dried in air at 125° C. for 1 hour followed by 250° C. for 1 hour. This procedure was repeated 3 times, and a total of 0.36 gram of insoluble ammonium tungstate was recovered following the last impregnation, to provide a net of 1.39 grams of ammonium tungstate impregnated onto the support. The above two-step drying procedure was used after each of the successive impregnations, except that after the fifth such impregnation the catalyst was additionally dried at 350° C. for 1 hour, followed by calcining at 500° C. for 3 hours, in air. In a subsequent impregnation, 5.4 cc. of an aqueous solution containing 0.58 gram of ammonium perrhenate were impregnated onto the catalyst, followed by drying at 125° C. for 1 hour, 202° C. for 1 hour, and 350° C. for 1 hour, and calcining at 500° C. for 3 hours, in air. The resulting oxide catalyst was found to contain 3.0 wt.% rhenium and 7.5 wt.% tungsten, calculated as the elements, based on the weight of the catalyst support. Ten cc. of the resulting catalyst was then mixed with 20 cc. of fused ceramic inerts (12–20 mesh) and tested as in Example 3, at the conditions summarized in Table VI, Run 1 below.

The oxide catalyst used in Run 1 was then sulfided using the procedure of Example 1(b), after which the sulfided catalyst was employed in Runs 2–4, using the conditions described in Table VI.

TABLE V

| Run No. | Time (hrs) | Temp. (°C.) | Press. psig | Gas Feed (cc/min.) | | | | GHSV (3) | Butene Conv. (%) | % Selectivities | | | | |
|---|---|---|---|---|---|---|---|---|---|---|---|---|---|---|
| | | | | (1) 1-Butene | $O_2/N_2$ (2) | $H_2O$ | $N_2$ | | | MEK (4) | $CO_2$ | CO | SBA (5) | $C_4SH$ (6) |
| 1 | 26.7 | 307 | 8.8 | 60 | 380 | 224 | 0 | 3984 | 4.5 | 38.9 | 42.9 | 10.7 | 3.3 | 0 |
| 2 | 27.3 | 309 | 8.7 | 30 | 170 | 224 | 0 | 2568 | 4.1 | 50.0 | 43.2 | 0 | 3.8 | 0 |
| 3 | 24.0 | 303 | 8.8 | 60 | 0 | 224 | 380 | 3984 | 1.8 | 92.2 | 0 | 0 | 7.8 | 0 |
| 4 | 24.6 | 307 | 8.8 | 60 | 0 | 224 | 380 | 3984 | 2.0 | 92.4 | 0 | 0 | 7.6 | 0 |
| 5 | 30.4 | 304 | 9.1 | 102 | 0 | 224 | 730 | 6336 | 1.6 | 96.1 | 0 | 0 | 3.1 | 0 |

(1) Feed = gas mixture containing 85 vol. % butene-1, 15 vol. % n-butane.
(2) Fed as 10 vol. % $O_2$ in $N_2$.
(3) Total gas hourly space velocity.
(4) Methyl ethyl ketone.
(5) Secondary butyl alcohol.
(6) Butyl mercaptan.

EXAMPLE 8

Using the procedure as described above for Example 1(a), 15 cc. of the gamma-alumina (12–20 mesh) was dried in air at 500° C. for 3 hours, to provide a dry

TABLE VI

| Run No. | Time (hrs) | Temp. (°C.) | Press. psig | Gas Feed (cc/min.) | | | | GHSV (3) | Butene Conv. (%) | % Selectivities | | | |
|---|---|---|---|---|---|---|---|---|---|---|---|---|---|
| | | | | (1) 1-Butene | O₂/N₂ (2) | H₂O | N₂ | | | MEK (4) | CO₂ | CO | SBA (5) |
| Rh—W Oxide | | | | | | | | | | | | | |
| 1 | 2.3 | 313 | 9.4 | 60 | 380 | 224 | 0 | 3984 | 5.0 | 51.0 | 3.1 | 4.7 | 34.5 |
| Re—W Sulfide | | | | | | | | | | | | | |
| 2 | 2.5 | 299 | 9.7 | 60 | 380 | 224 | 0 | 3984 | 2.1 | 40.5 | 3.8 | 7.7 | 31.0 |
| 3 | 3.5 | 306 | 9.5 | 60 | 0 | 224 | 380 | 3984 | 1.5 | 53.1 | 0 | 0 | 46.9 |
| 4 | 4.0 | 374 | 9.7 | 60 | 0 | 224 | 380 | 3984 | 3.1 | 88.9 | 0 | 0 | 9.2 |

(1) Feed = gas mixture containing 85 vol. % butene-1, 15 vol. % n-butane.
(2) Fed as 10 vol. % O₂ in N₂.
(3) Total gas hourly space velocity.
(4) Methyl ethyl ketone.
(5) Secondary butyl alcohol.

EXAMPLE 9

The catalyst preparation and sulfiding procedure of Example 5 was repeated (except that the reactor was loaded with 30 cc. of the oxide catalyst prior to the in situ sulfiding step, and no solid inerts were admixed therewith), to prepare a sulfide catalyst, supported on gamma-alumina, comprising 0.5 wt.% Rh, 3.7 wt.% Re and 9.5 wt.% Mo, calculated as the respective element. The catalyst was then used in a first series of runs, using N₂ in the gas feed (Runs 1-4) and then was used in another series of runs (Runs 5-8) in which no N₂ was fed to the reactor. The data thereby obtained is set forth in Table VII below. These runs indicate the excellent stability and activity properties of the catalysts of this invention.

TABLE VII

| Run No. | Time (hrs) | Temp. (°C.) | Press. psig | Gas Feed (cc/min.) | | | GHSV (3) | Butene Conv. (%) | % Selectivities | | | |
|---|---|---|---|---|---|---|---|---|---|---|---|---|
| | | | | Butene (1) | N₂ (2) | H₂O | | | MEK (4) | CO₂ | CO | SBA (5) |
| 1 | 11.5 | 357 | 20.6 | 60 | 380 | 224 | 3984 | 4.1 | 97.0 | 0 | 0 | 0.7 |
| 2 | 12.1 | 370 | 8.7 | 60 | 380 | 224 | 3984 | 4.3 | 97.0 | 0 | 0 | 0.5 |
| 3 | 12.8 | 359 | 8.9 | 60 | 380 | 224 | 3984 | 3.8 | 98.1 | 0 | 0 | 0.5 |
| 4 | 13.3 | 368 | 9.0 | 60 | 380 | 224 | 3984 | 3.9 | 96.7 | 0 | 0 | 0.8 |
| 5 | 19.6 | 367 | 8.0 | 60 | 0 | 224 | 1704 | 4.4 | 98.8 | 0 | 0 | 0.7 |
| 6 | 20.4 | 370 | 8.0 | 60 | 0 | 224 | 1704 | 4.3 | 98.6 | 0 | 0 | 1.1 |
| 7 | 20.9 | 366 | 7.9 | 60 | 0 | 224 | 1704 | 4.5 | 96.6 | 0 | 0 | 2.7 |
| 8 | 22.1 | 367 | 8.9 | 60 | 0 | 224 | 1704 | 4.4 | 98.4 | 0 | 0 | 1.2 |

(1) Feed = gas mixture containing 85 vol. % butene-1 and 15 vol. % iso-butane.
(2) Fed as N₂.
(3) Total gas hourly space velocity.
(4) Methyl ethyl ketone.
(5) Secondary butyl alcohol.

EXAMPLE 10

Following the procedure of Example 1(a), 35 cc. of dried gamma-alumina (Alfa Product) was sequentially impregnated with Mo (using 12.0 cc. of aqueous solution containing 5.2 grams of ammonium permolybdate), Re (using 11.9 cc. of an aqueous solution containing 1.64 grams of ammonium perrhenate) and finally by Rh (using 11.9 cc. of an aqueous solution containing 0.422 gram of rhodium trinitrate). After each impregnation, the solids are dried under air and then calcined, using the procedure of Example 1(a). The resulting oxide catalyst was found to comprise 0.5 wt.% Rh, 3.7 wt.% Re, and 9.7 wt.% Mo, calculated as the respective elements, based on the total weight of the support. The oxide catalyst was then sulfided using the procedure of Example 1(b), except that the catalyst was not mixed with inerts (instead, 30 cc. of the oxide catalyst was placed in the vessel for sulfiding), and except that the sulfiding step was carried out for a period of 9.0 hours. The resulting sulfided catalyst was employed in a series of runs following the procedure of Comparative Example 2, using conditions set forth in Table VIII.

EXAMPLE 11

The catalyst preparation procedure of Example 10 was repeated employing 45 cc. of the dried gamma-alumina (Alfa Product) which was sequentially impregnated with 15.1 cc. of an aqueous solution containing 6.58 grams of ammonium permolbdate, 15.1 cc. of an aqueous solution containing 2.05 gram of ammonium perrhenate and 15.1 cc. of an aqueous solution containing 0.534 gram rhodium trinitrate. The drying and calcining procedure of Example 10 was used after each impregnation. Thereafter, the dried catalyst was subjected to an additional impregnation, sequentially, with 13.2 cc. of an aqueous solution containing 1.77 grams of ammonium perrhenate followed by 12.5 cc. of an aqueous solution containing 1.46 grams of rhodium trinitrate. Again, the drying and calcining procedure of Example 10 was formed after each impregnation. The resulting oxide catalyst was found to comprise 2.1 wt.% Rh, 7.4 wt.% Re and 9.5 wt.% Mo. Thirty cc. of this catalyst was then sulfided using the procedure of Example 10 and employed in a series of runs following the procedure of Comparative Example 2 using the conditions set forth in Table VIII.

TABLE VIII

| Run No. | Time (hrs) | Temp. (°C.) | Press. psig | Gas Feed (cc/min.) Butene (1) | H₂O | N₂ | GHSV (2) | Butene Conv. (%) | % Selectivities MEK | CO₂ | CO | SBA | Others |
| --- | --- | --- | --- | --- | --- | --- | --- | --- | --- | --- | --- | --- | --- |
| 10A | 3.0 | 375 | 9.3 | 60 | 224 | 380 | 1328 | 5.1 | 95.5 | 0 | 0 | 0.7 | 3.8 |
| 10B | 8.0 | 375 | 9.0 | 60 | 224 | 60 | 688 | 5.1 | 96.7 | 0 | 0 | 0.7 | 2.6 |
| 10C | 14.0 | 375 | 9.0 | 60 | 224 | 60 | 688 | 3.2 | 97.1 | 0 | 0 | 0.5 | 2.3 |
| 11A | 3.0 | 300 | 9.6 | 60 | 224 | 60 | 688 | 3.7 | 98.3 | 0 | 0 | 1.1 | 0.7 |
| 11B | 6.1 | 375 | 9.6 | 60 | 224 | 60 | 688 | 6.5 | 95.9 | 0 | 0 | 0.8 | 3.3 |
| 11C | 9.8 | 375 | 9.6 | 30 | 224 | 60 | 688 | 8.4 | 95.1 | 0 | 0 | 0.7 | 4.2 |
| 11D | 13.5 | 375 | 9.3 | 30 | 224 | 0 | 508 | 7.6 | 98.4 | 0 | 0 | 0.5 | 1.1 |
| 11E | 18.9 | 375 | 9.9 | 30 | 224 | 0 | 508 | 6.9 | 96.6 | 0 | 0 | 0.6 | 2.8 |

(1) Feed = gas mixture containing 85 vol. % butene-1 and 15 vol. % iso-butane.
(2) Gas hourly space velocity (cc feed/cc catalyst/hour).

EXAMPLE 12

Following the catalyst preparation procedure of Example 10, 35 cc. of dried gamma-alumina (UCI-L-1278) was sequentially impregnated with 14.0 cc. of an aqueous solution containing 3.93 grams of ammonium permolybdate, 13.5 cc. of an aqueous solution containing 1.214 grams of ammonium perrhenate, 13.5 cc. of an aqueous solution containing 1.17 grams of ammonium perrhenate and finally by 13.5 cc. of an aqueous solution containing 1.262 grams of rhodium trinitrate. The resulting oxide catalyst, after the repetitive air drying and calcining after each impregnation, was found to comprise 2.0 wt.% Rh, 7.4 wt.% Re and 9.5 wt.% Mo. This oxide catalyst was then sulfided using the conditions of Example 10 (30 cc. of catalyst, no inerts, 9 hours) and the trimetallic sulfide catalyst was then employed in a series of runs using the conditions set forth in Table IX and following the procedure of Comparative Example 2.

catalyst was then employed in a series of runs using the conditions set forth below in Table IX and following the procedure of Comparative Example 2.

TABLE IX

| Run No. | Time (hrs) | Temp. (°C.) | Press. psig | Gas Feed (cc/min.) Butene (1) | H₂O | GHSV (2) | Butene Conv. (%) | % Selectivities MEK | CO₂ | CO | SBA | Others |
| --- | --- | --- | --- | --- | --- | --- | --- | --- | --- | --- | --- | --- |
| 12A | 21.5 | 375 | 280 | 122 | 229 | 702 | 9.4 | 96.0 | 0 | 0 | 1.6 | 2.4 |
| 12B | 24.5 | 375 | 280 | 122 | 482 | 1208 | 10.8 | 94.6 | 0 | 0 | 2.0 | 3.5 |
| 13A | 5.8 | 375 | 286 | 92 | 482 | 1148 | 13.4 | 92.2 | 0 | 0 | 1.9 | 6.0 |
| 13B | 9.3 | 375 | 286 | 92 | 482 | 1148 | 12.1 | 95.1 | 0 | 0 | 1.7 | 3.3 |
| 13C | 13.5 | 375 | 9 | 93 | 482 | 1150 | 1.7 | 95.9 | 0 | 0 | 1.4 | 2.7 |
| 13D | 18.5 | 375 | 800 | 121 | 482 | 1206 | 12.9 | 94.7 | 0 | 0 | 2.0 | 3.3 |
| 13E | 21.5 | 375 | 800 | 121 | 482 | 1206 | 10.2 | 95.7 | 0 | 0 | 2.2 | 2.1 |

(1) 99+% butene-1. No N₂ was used in the feed to the reactor in these runs.
(2) Gas hourly space velocity (cc feed/cc catalyst/hour at STP).

EXAMPLE 13

The catalyst preparation procedure of Example 10 was repeated employing 35 cc. of dried gamma-alumina (Alfa Product) and sequential impregnation, followed by intermediate air drying and calcining, using impregnation with 12.0 cc. of an aqueous solution containing 5.25 grams of ammonium permolybdate, 12.0 cc. of an aqueous solution containing 1.61 grams of ammonium perrhenate and 12.0 cc. of an aqueous solution containing 0.837 gram of ammonium trinitrate. The resulting oxide catalyst was found to comprise 1.0 wt.% Rh, 3.7 wt.% Re, and 9.5 wt.% Mo. This oxide catalyst was then sulfided using the procedure of Example 10 (30 cc. catalyst, no inerts, 9 hours), and the sulfided trimetallic

EXAMPLE 14

The procedure of Example 9 is repeated in two separate runs employing the Rh-Re-Mo sulfide catalyst except that the gas feed to the reactor comprised 60 cc./min. cis-butene-2, 380 cc./min. N₂ and 224 cc./min. water vapor, at a pressure of 8.0 psig at the selected temperatures and for the selected period of times, providing the following deserved results:
Run 1: 372° C., 4.1 hrs.—3.5% butene-2 conversion, 95.9% MEK selectivity, 1.1% SBA selectivity.
Run 2: 376° C., 5.2 hrs.—3.8% butene-2 conversion, 96.6% MEK selectivity, 1.4% SBA selectivity.
No CO₂ or CO by-products were detected.

EXAMPLE 15

The catalyst vacuum impregnation procedure of Example 1(a) was repeated, except that no Pd salt was employed and the following calculated aqueous solutions of ammonium paramolybdate and ammonium perrhenate were used to sequentially impregnate 37.0 cc. of the gamma-alumina; 12.0 cc. of an aqueous solution contains 5.24 gms. of ammonium paramolybdate; 12.0 cc. of an aqueous solution containing 1.63 grams of ammonium perrhenate. The resulting Re-Mo oxide catalyst was then sulfided using the procedure of Example 1(b) and employed in a series of runs for MEK formation from butene-1 as summarized in Table X below. The catalyst comprised 3.7 wt.% Re and 9.7 wt.% Mo, calculated as the elements. No CO₂ or CO was detected in any run.

TABLE X

| Run No. | Time (hrs) | Temp. (°C.) | Press. psig | Gas Feed (cc/min.) Butene (1) | H$_2$O | N$_2$ | GHSV (2) | Butene Conv. (%) | % Selectivities MEK | CO$_2$ | CO | SBA | Others |
|---|---|---|---|---|---|---|---|---|---|---|---|---|---|
| 1 | 0.6 | 371 | 8.7 | 60 | 224 | 380 | 3984 | 2.5 | 92.5 | 0 | 0 | 0 | 9.5 |
| 2 | 2.1 | 374 | 9.3 | 60 | 224 | 380 | 3984 | 2.4 | 96.7 | 0 | 0 | 0.5 | 2.8 |
| 3 | 2.7 | 365 | 9.3 | 60 | 224 | 380 | 3984 | 3.0 | 98.2 | 0 | 0 | 0.2 | 1.5 |
| 4 | 7.8 | 314 | 8.0 | 60 | 224 | 380 | 3984 | 2.3 | 99.0 | 0 | 0 | 1.0 | — |
| 5 | 10.0 | 369 | 8.0 | 60 | 224 | 380 | 3984 | 2.3 | 98.6 | 0 | 0 | 0.5 | 0.9 |

(1) 99+% butene-1.
(2) Gas hourly space velocity (cc feed/cc catalyst/hour).

EXAMPLE 16

The Re-Mo sulfide catalyst of Example 15 was employed in a series of experiments to illustrate the adverse affect of butadiene in a butene-1 feed to the process of this invention. In a first run the catalyst is contacted with a butene-1 feed comprising essentially pure butene-1 (99+% butene-1) in the absence of any butadiene and high selectivities to MEK and a high selectivity to MEK was observed, as summarized for run No. 1 in Table XI below. Thereafter, butadiene was substituted for butene-1 (butadiene feed rate=60 cc/min.) for a total time of 1.2 hours at a temperature of about 375° C. and a pressure of about 9.0 psig. After 0.7 hours, about 10% of the butadiene was converted to product and methyl vinyl ketone was formed in a selectivity of about 23%. After about 1.2 hours, the butadiene conversion dropped to about 3% during the interval of 0.7 to 1.2 hours, and methyl vinyl ketone selectivity was found to be 26%. The thus-treated catalyst was then contacted in a second run (Run No. 2) with a fresh butene-1 feed. After one hour, only trace amounts of methyl ethyl ketone were found using the conditions summarized in Table X.

To illustrate the catalyst rejuvenation procedure of this invention, the feed to the reactor was changed to comprise 380 cc/hr. of a 10:90 vol:vol oxygen/nitrogen mixture at a temperature of 375° C., which was passed over the catalyst at 1.0 hour. Thereafter, the resulting Re-Mo oxide catalyst was sulfided with a gas mixture comprising 190 cc./min. of hydrogen sulfide (6 vol.% in nitrogen), and 220 cc./min. hydrogen at a temperature of 375° C. for 1 hour, followed by purging of the sulfided catalyst to remove excess H$_2$S with 500 cc./hr. of hydrogen at 375° C. for ½ hour. Following this rejuvenation procedure the catalyst was again exposed to a fresh butene-1 feed in Runs No. 3, 4 and 5, which is summarized in Table XI. In this run, the rejuvenated catalyst was found to be again capable of forming high selectivities of the desired methyl ethyl ketone from the butene-1.

TABLE XI

| Run No. | Time (hrs) | Temp. (°C.) | Press. psig | Gas Feed (cc/min.) Butene (1) | H$_2$O | N$_2$ | GHSV (2) | Butene Conv. (%) | % Selectivities MEK | CO$_2$ | CO | SBA | Others |
|---|---|---|---|---|---|---|---|---|---|---|---|---|---|
| 1 | 2.7 | 383 | 9.0 | 60 | 224 | 380 | 3984 | 2.3 | 98.9 | 0 | 0 | 1.1 | — |
| 2 | 1.0 | 375 | 9.0 | 60 | 224 | 380 | 3984 | <0.1 | trace | — | — | — | — |
| 3 | 0.7 | 382 | 8.9 | 60 | 224 | 380 | 3984 | 3.0 | 93.3 | 0 | 0 | 0.6 | 6.1 |
| 4 | 1.8 | 379 | 8.9 | 60 | 224 | 380 | 3984 | 1.8 | 95.9 | 0 | 0 | 0.6 | 3.5 |
| 5 | 2.3 | 384 | 8.6 | 60 | 224 | 380 | 3984 | 1.8 | 96.6 | 0 | 0 | 0.5 | 2.8 |

(1) 99+% butene-1.
(2) Gas hourly space velocity (cc feed/cc catalyst/hour).

EXAMPLE 17

To illustrate the formation of acetone from propylene, the Rh-Re-Mo sulfide catalyst prepared as in Example 14 was tested at the conditions summarized in Table XII and high selectivities to acetone were observed.

TABLE XII

| Time (hrs) | Press. psig | Temp. (°C.) | Gas Feed (cc/min.) Propylene | N$_2$ | H$_2$O | GHSV (1) | Propylene Conv. (%) | Selectivities Acetone | CO$_2$ | CO | IPA (2) | Others |
|---|---|---|---|---|---|---|---|---|---|---|---|---|
| 2.2 | 9.3 | 369 | 60 | 380 | 224 | 1328 | 7.4 | 99.5 | 0 | 0 | Trace | 0.5 |
| 5.0 | 9.3 | 369 | 60 | 380 | 224 | 1328 | 7.1 | 99.4 | 0 | 0 | Trace | 0.6 |
| 7.2 | 8.6 | 371 | 60 | 380 | 224 | 1328 | 9.7 | 91.7 | 0 | 0 | 7.6 | 0.7 |
| 9.5 | 8.6 | 371 | 60 | 380 | 224 | 1328 | 11.7 | 99.7 | 0 | 0 | Trace | 0.3 |
| 10.0 | 8.7 | 375 | 60 | 380 | 224 | 1328 | 8.2 | 98.7 | 0 | 0 | 1.2 | 0.1 |
| 11.0 | 6.1 | 371 | 60 | 0 | 224 | 568 | 12.3 | 85.8 | 0 | 0 | Trace | 14.2 |
| 12.8 | 6.9 | 372 | 60 | 0 | 224 | 568 | 12.7 | 91.0 | 0 | 0 | 2.5 | 6.5 |
| 13.3 | 6.9 | 369 | 60 | 0 | 224 | 568 | 15.3 | 96.1 | 0 | 0 | 3.5 | 0.4 |

(1) Gas hourly space velocity (cc feed/cc catalyst/hour).
(2) IPA = isopropyl alcohol.

EXAMPLE 18

To illustrate the selective conversion of cyclohexene to cyclohexanone, a series of runs are performed in which a gaseous mixture containing cyclohexene, nitrogen and water vapor is contacted with a Re-Rh-Mo sulfided catalyst prepared as in Example 14, and employing the conditions summarized below in Table XIII. The data thereby obtained are also set forth in Table XIII.

TABLE XIII

| Time (min) | Press. (psig) | Temp. (°C.) | Feed Rate (cc/min.) | | | GHSV (1) | Cyclohexene Conv. (%) | Selectivity (%) | |
|---|---|---|---|---|---|---|---|---|---|
| | | | $N_2$ | $H_2O$ | Cyclohexene | | | $CO_2$ | Cyclohexanone |
| 15 | 18 | 297 | 167 | 236 | 41 | 2664 | 2.1 | — | 1.9 |
| 30 | 18 | 303 | 167 | 286 | 38 | 2946 | 1.9 | — | 24.1 |
| 60 | 18 | 302 | 167 | 236 | 37 | 2640 | 1.9 | — | 15.5 |
| 90 | 18 | 302 | 167 | 224 | 45 | 2616 | 2.0 | — | 17.1 |

(1) Gas hourly space velocity (cc/cc/hr)

In each of the foregoing examples, illustrative of the process of this invention, butane by-product was observed to be formed from the butene feeds in selectivities of less than about 0.5 mol.%, based on the butene fed to the reactor. Thus, the improved process of this invention allows the formation of the desired ketone in the substantial absence of olefin hydrogenation by-products, that is, the hydrogenation by-products will be generally formed in a selectivity of less than about 1 mol.%, based on the olefin fed.

Preferably, monoolefin feeds to the process of this invention are substantially free (e.g., contain less than 1 wt.%) of diolefins or acetylenic hydrocarbons to obtain the highest catalyst activity to form the ketones corresponding to the monoolefin feeds.

It will be obvious that various changes and modifications may be made without departing from the invention and it is intended, therefore, that all matter contained in the foregoing description shall be interpreted as illustrative only and not limitative of the invention.

What is claimed is:

1. A process for preparing ketones in high selectivity which comprises contacting the corresponding olefin in the gaseous phase with water vapor in an oxygen-free reaction zone at elevated temperature in the presence of a catalyst comprising rhenium sulfide, said olefin comprising at least one member selected from the group consisting of linear mono-olefins of from 2 to 20 carbon atoms and cyclic mono-olefins of from 3 to 20 carbon atoms.

2. The process according to claim 1 wherein said catalyst additionally comprises at least one promoter selected from the group consisting of sulfides of Group VIB and Group VIII noble metals.

3. The process according to claim 1 wherein said catalyst comprises a mixture of (1) a sulfide of Re, (2) a sulfide of Cr, Mo or W, and (3) a sulfide of Ru, Rh, Pd, Os, Ir or Pt.

4. The process according to claim 1 wherein said olefin comprises an alkene of from 4 to 10 carbon atoms or a cycloalkene of from 4 to 10 carbon atoms.

5. The process according to claim 1 wherein the catalyst is supported on gamma-alumina.

6. A process for converting an olefin selected from the group consisting of alkenes having from 4 to 10 carbon atoms and cycloalkenes having from 4 to 10 carbon atoms into the corresponding ketone, which comprises contacting said olefin in the gaseous phase with water vapor in an oxygen-free reaction zone in the presence of a solid catalyst comprising rhenium sulfide, at a temperature of from about 125° to 600° C. and at pressures of from about 0 to 2000 psig.

7. The process according to claim 6 wherein said water vapor and said olefin are introduced into said reaction zone in a molar ratio of olefin:water vapor of from about 2:1 to 1:20.

8. The process according to claim 6 wherein said catalyst additionally comprises at least one promoter selected from the group consisting of sulfides of Cr, Mo, W, Ru, Rh, Pd, Os, Ir and Pt.

9. The process according to claim 7 wherein said temperature is from 200° to 400° C., and said olefin and water vapor are contacted at a gas hourly space velocity through the reaction zone of from 100 to 10,000 v/v/hour.

10. The process according to claim 7 wherein said olefin comprises butene-1 and said ketone comprises methyl ethyl ketone.

* * * * *